United States Patent [19]

Brandes et al.

[11] Patent Number: 4,537,905
[45] Date of Patent: Aug. 27, 1985

[54] FUNGICIDALLY ACTIVE SUBSTITUTED OXIMINOACETANILIDES

[75] Inventors: Wilhelm Brandes, Leichlingen; Werner Daum, Krefeld, both of Fed. Rep. of Germany

[73] Assignee: Bayer Aktiengesellschaft, Leverkusen, Fed. Rep. of Germany

[21] Appl. No.: 461,304

[22] Filed: Jan. 27, 1983

[30] Foreign Application Priority Data

Feb. 20, 1982 [DE] Fed. Rep. of Germany ....... 3206235

[51] Int. Cl.³ .................... A01N 37/34; A01N 43/64; C07C 121/84; C07D 249/08
[52] U.S. Cl. ................ 514/521; 260/465 D; 260/455 R; 514/303; 514/373; 514/383; 514/406; 514/452; 514/472; 514/513; 546/121; 548/262; 548/378; 549/321; 549/373
[58] Field of Search .............. 548/262, 336, 341, 378; 424/269, 273 R, 273 P, 278, 279, 301, 304, 256; 260/455 R, 465 D; 549/321, 373, 452; 546/121

[56] References Cited

U.S. PATENT DOCUMENTS

| | | | |
|---|---|---|---|
| 4,032,657 | 6/1977 | Moser | 560/43 |
| 4,178,383 | 12/1979 | Brandes et al. | 260/465 D |
| 4,188,401 | 2/1980 | Brandes et al. | 260/465 D |
| 4,330,556 | 5/1982 | Hubele | 260/465 D |
| 4,438,125 | 3/1984 | Hubele et al. | 548/262 |
| 4,478,848 | 10/1984 | Brandes et al. | 260/465 D |

FOREIGN PATENT DOCUMENTS

| | | |
|---|---|---|
| 0000023 | 12/1978 | European Pat. Off. |
| 0011047 | 5/1980 | European Pat. Off. |
| 0020859 | 1/1981 | European Pat. Off. |
| 2312956 | 9/1973 | Fed. Rep. of Germany |

OTHER PUBLICATIONS

Formigoni et al., Chem. Abstracts, vol. 92, Abstract No. 123424y, (1980).

*Primary Examiner*—Alton D. Rollins
*Attorney, Agent, or Firm*—Sprung Horn Kramer & Woods

[57] ABSTRACT

Substituted oximinoacetanilides of the general formula

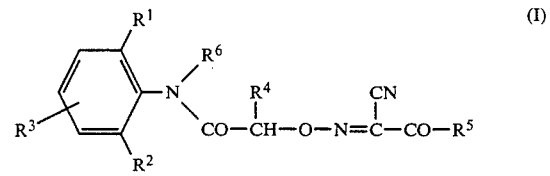

in which
$R^1$ denotes an alkyl or alkoxy group or a halogen atom,
$R^2$ denotes a hydrogen or halogen atom or an alkyl or trifluoromethyl group,
$R^3$ denotes a hydrogen or halogen atom or an alkyl group,
$R^4$ denotes a hydrogen atom or a methyl group,
$R^5$ denotes an alkoxy, amino or —NH—CO—NH—$R^7$ group,
wherein
$R^7$ represents a hydrogen atom or an optionally cyano-, alkoxy- or alkoxycarbonyl-substituted alkyl group, or represents a cycloalkyl group, and
$R^6$ denotes various aliphatic or heterocyclic radicals, are new and find use as pest-combating agents, in particular as fungicides.

7 Claims, No Drawings

FUNGICIDALLY ACTIVE SUBSTITUTED OXIMINOACETANILIDES

The present invention relates to certain new substituted oximinoacetanilides, to processes for their production and to their use as pest-combating agents, in particular as fungicides.

As has already been known for a long time, fungicides are used for plant protection in agriculture and in horticulture, in particular zinc ethylene-1,2-bis-dithiocarbamate and N-trichloromethylthio-tetrahydrophthalimide; among the commercial products, the compounds mentioned are very important (see R. Wegler, "Chemie der Pflanzenschutzund Schädlingsbekämpfungsmittel" (Chemistry of Plant Protection Agents and Pest-Combating Agents), Volume 2, pages 65 and 108, Berlin/Heidelberg/New York (1970)). However, the action is not always completely satisfactory when low concentrations are used.

Furthermore, it has been disclosed that some isonitroso-cyanoacetamide derivatives (DE-OS (German Published Specification) No. 2,312,956 and U.S. Pat. Nos. 3,919,284, 3,957,847 and 4,188,401) and alkoxycarbonylethyl-N-haloacetylanilines (DE-OS (German Published Specification) No. 2,350,944) possess fungicidal properties. In these cases, also, the activity is not always satisfactory when low amounts are used, and damage to plants can occur at relatively high concentrations.

The present invention now provides, as new compounds, the substituted oximinoacetanilides of the general formula

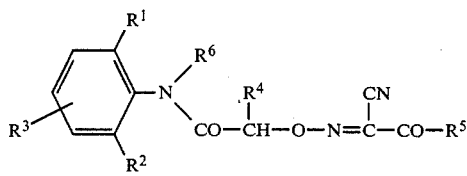

in which
R$^1$ denotes an alkyl or alkoxy group or a halogen atom,
R$^2$ denotes a hydrogen or halogen atom or an alkyl or trifluoromethyl group,
R$^3$ denotes a hydrogen or halogen atom or an alkyl group,
R$^4$ denotes a hydrogen atom or a methyl group,
R$^5$ denotes an alkoxy, amino or —NH—CO—NH—R$^7$ group, wherein
R$^7$ represents a hydrogen atom or an optionally cyano-, alkoxy- or alkoxycarbonyl-substituted alkyl group or represents a cycloalkyl group, and
R$^6$ denotes an alkinyl, alkoxyalkyl, halogenoalkoxyalkyl, cyanoalkoxyalkyl, cycloalkoxyalkyl, alkenoxyalkyl, alkinoxyalkyl, alkylthioalkyl, alkylcarbonylalkyl, alkoxycarbonylalkyl or alkylthiocarbonylalkyl group; denotes an aminocarbonylalkyl group, the amino group thereof being optionally substituted by alkyl radical(s) which, together with the nitrogen atom, can also form a heterocyclic ring; denotes a 5-membered or 6-membered heterocyclylalkyl radical which is bonded via C or N and which can contain up to 3 nitrogen atoms, up to 2 oxygen atoms, or up to 2 nitrogen atoms and 1 oxygen atom; denotes a bicycloheterocyclylalkyl radical having up to 3 nitrogen atoms, it being possible for the heterocyclic radicals to be further substituted by alkyl groups or the keto group; denotes a hydrogenated furanone radical which is optionally substituted by one or more alkyl groups; or denotes a radical of the general formula

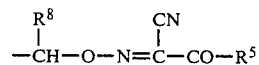

wherein
R$^5$ has the above meaning and
R$^8$ represents a hydrogen atom or a methyl or ethyl group.

The substituted oximinoacetanilides according to the invention, of the general formula (I), can be present in various stereochemical forms. Formula (I) embraces all possible forms and their mixtures.

The invention further relates to a process for the production of a compound of the invention, characterized in that (a) a substituted acetanilide of the general formula

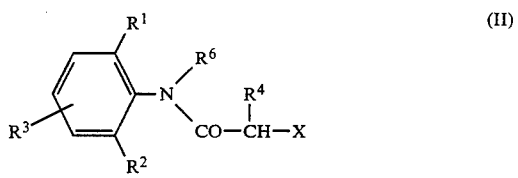

in which
R$^1$, R$^2$, R$^3$, R$^4$ and R$^6$ have the above meanings and
X represents a chlorine, bromine or iodine atom or a sulphonyloxy radical,
is reacted with a 2-cyano-2-oximinoacetic acid derivative of the general formula

in which R$^5$ has the above meaning, if appropriate in a diluent in the form of the alkali metal salt or alkaline earth metal salt thereof or in the presence of a proton acceptor, or (b) in the case in which R$^5$ represents a —NH—CO—NHR$^9$ group and
R$^9$ represents an optionally cyano-, alkoxy- or alkoxycarbonyl-substituted alkyl radical, or represents a cycloalkyl radical, but R$^6$ does not represent a

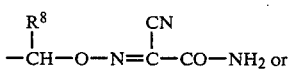

or

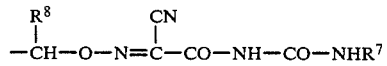

group, a compound of the general formula

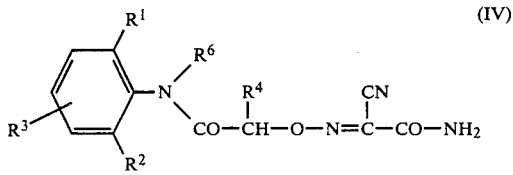

in which $R^1$, $R^2$, $R^3$ and $R^4$ have the above meanings, and $R^6$ has the abovementioned meaning but does not represent a

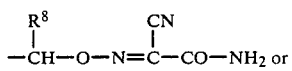 or

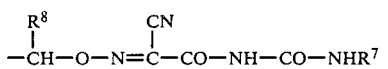

group, in the presence of a base, is reacted with an isocyanate of the general formula $$OCN—R^9 \qquad (V)$$

in which $R^9$ has the above meaning, if appropriate in the presence of a diluent, or (c) in the case in which $R^6$ represents a

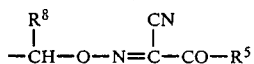

group and $R^5$ is identical at each occurrence, a compound of the general formula

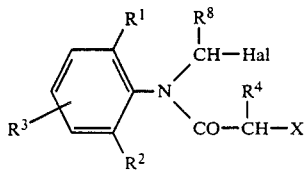

$R^1$, $R^2$, $R^3$, $R^4$, $R^8$ and X have the above meanings and

Hal represents a halogen atom, preferably a chlorine atom, is reacted with 2 mols of a 2-cyano-2-oximinoacetic acid derivative of the formula (III), if appropriate in a diluent in the form of the alkali metal salt or alkaline earth metal salt thereof or in the presence of a proton acceptor.

The new substituted oximinoacetanilides of the formula (I) possess powerful fungicidal properties. They may be used protectively, curatively and eradicatively. In addition, they have systemic and/or locosystemic properties. Surprisingly, they are better tolerated by plants than are the known isonitrosocyanoacetamide derivatives. Compared with the dithiocarbamates and N-trichloromethylthio-tetrahydrophthalimide, they have the advantage of a curative and eradicative action.

Because of the many possible uses of their superior biological properties, the compounds according to the invention represent a valuable enrichment of the art.

A further important viewpoint of this invention is the fact that new active compounds having properties which are valuable in practice are being made available at a time when older active compounds are becoming useless commercially as a result of signs of resistance.

There is therefore a definite need, today and in the foreseeable future, for new fungicides.

Of the substituted oximinoacetanilides according to the invention, of the formula (I), those are preferred in which $R^1$ denotes a $C_1$ to $C_4$ alkyl or $C_1$ to $C_4$ alkoxy group or a halogen atom, $R^2$ denotes a hydrogen or halogen atom or a $C_1$ to $C_4$ alkyl or trifluoromethyl group, $R^3$ denotes a hydrogen or halogen atom or a methyl group, $R^4$ denotes a hydrogen atom or a methyl group, $R^5$ denotes a $C_1$ to $C_4$ alkoxy, amino or —NH—CO—NH—$R^7$ group, wherein $R^7$ represents a hydrogen atom or an optionally cyano-, $C_1$ to $C_4$ alkoxy- or $C_1$ to $C_4$ alkoxycarbonyl-substituted $C_1$ to $C_5$ alkyl group, or represents a $C_3$ to $C_6$ cycloalkyl group, and $R^6$ denotes a $C_3$ to $C_5$ alkinyl, $C_1$ to $C_4$ alkoxy-$C_1$ to $C_3$ alkyl, halogeno-$C_1$ to $C_4$ alkoxy-$C_1$ to $C_3$ alkyl, cyano-$C_1$ to $C_4$ alkoxy-$C_1$ to $C_3$ alkyl, $C_4$ to $C_7$ cycloalkoxy-$C_1$ to $C_3$ alkyl, $C_2$ to $C_4$ alkenoxy-$C_1$ to $C_3$ alkyl, $C_2$ to $C_4$ alkinoxy-$C_1$ to $C_3$ alkyl, $C_1$ to $C_4$ alkylthio-$C_1$ to $C_3$ alkyl, ($C_1$ to $C_4$ alkyl)-carbonyl-$C_1$ to $C_3$ alkyl, ($C_1$ to $C_4$ alkoxy)-carbonyl-$C_1$ to $C_3$ alkyl or ($C_1$ to $C_4$ alkylthio)-carbonyl-$C_1$ to $C_3$ alkyl group; denotes an aminocarbonyl-$C_1$ to $C_3$ alkyl group, wherein the amino group thereof is optionally substituted by 1 or 2 $C_1$ to $C_3$ alkyl radicals which, together with the nitrogen atom, can also form a heterocyclic ring; denotes a 5-membered or 6-membered heterocyclyl-$C_1$ to $C_4$ alkyl radical which is bonded via C or N and can contain up to 3 nitrogen atoms, up to 2 oxygen atoms or up to 2 nitrogen atoms and 1 oxygen atom; denotes a bicycloheterocyclylalkyl radical having up to 3 nitrogen atoms, it being possible for the heterocyclic radicals to be substituted by $C_1$ or $C_2$ alkyl or a keto group; denotes a hydrogenated furanone radical which is optionally substituted by alkyl group(s); or denotes a radical of the general formula $$\overset{R^8}{\underset{|}{-CH}}-O-N=\overset{CN}{\underset{|}{C}}-CO-R^5$$

wherein $R^5$ has the meaning given immediately above and $R^8$ represents a hydrogen atom or a methyl or ethyl group.

Of the substituted oximinoacetanilides according to the invention, of the formula (I), those are particularly preferred in which $R^1$ represents an alkyl group having 1 to 4 carbon atoms (especially methyl and ethyl) or an alkoxy group having 1 to 4 carbon atoms (such as methoxy or ethoxy) or a chlorine atom, $R^2$ represents a hydrogen atom, an alkyl group having 1 to 4 carbon atoms (especially methyl or ethyl) or a chlorine atom, $R^3$ and $R^4$ represent hydrogen atoms, $R^5$ represents an alkoxy group having 1 to 3 carbon atoms or represents an amine group, and $R^6$ denotes a $C_3$ to $C_5$ alkinyl, $C_1$ to $C_4$ alkoxy-$C_1$ to $C_3$ alkyl, $C_1$ to $C_4$ alkylthio-$C_1$ to $C_3$ alkyl, halogeno-$C_1$ to $C_4$ alkoxy-$C_1$ to $C_3$ alkyl, cyano-$C_1$ to $C_3$ alkoxy-$C_1$ to $C_3$ alkyl, $C_4$ to $C_7$ cycloalkoxy-$C_1$ to $C_3$ alkyl, $C_2$ to $C_4$ alkenoxy-$C_1$ to $C_3$ alkyl, $C_2$ to $C_4$ alkinoxy-$C_1$ to $C_3$ alkyl, methylcarbonyl-methyl, methoxycarbonyl-$C_1$ to $C_3$ alkyl or methylthiocarbonyl-$C_1$ to $C_3$ alkyl group; denotes an aminocarbonyl-$C_1$ to $C_3$ alkyl group wherein the amino group thereof is optionally substituted by 1 or 2 methyl radicals or can be a part of a 5-membered or 6-membered heterocyclic ring; denotes a 5-membered or 6-membered heterocyclyl-$C_1$ to $C_4$ alkyl radical which is bonded via C or N and can contain up to 3 nitrogen atoms, up to 2 oxygen atoms or up to 2 nitrogen atoms and 1 oxygen atom; denotes a bicycloheterocyclyl-$C_1$ to $C_4$ alkyl radical having up to 3 nitrogen atoms, it being possible for the heterocyclic radicals to be further substituted by methyl, ethyl or the keto group; or denotes a hydrogenated furanone radical or a methoxycarbonyl-(cyano)-methyleneiminoxymethyl or aminocarbonyl-(cyano)-methyleneiminoxymethyl radical.

The optionally substituted radicals mentioned can be monosubstituted or polysubstituted by identical or different substituents.

In addition to the compounds according to the invention which are mentioned in the preparative examples, the following further compounds according to the invention, of the general formula (I), may be mentioned as examples:

| $R^1$ | $R^2$ | $R^3$ | $R^4$ | $R^5$ | $R^6$ |
|---|---|---|---|---|---|
| $CH_3$ | $CH_3$ | H | H | $OC_4H_9$—n | $CH_2$—$OC_2H_5$ |
| $CH_3$ | $CH_3$ | H | $CH_3$ | $OC_4H_9$—n | $CH_2$—$OC_2H_5$ |
| $CH_3$ | $CH_3$ | H | H | $NH_2$ | $CH_2$—O—$CH_2$—$CH(CH_3)_2$ |
| $CH_3$ | $CH_3$ | H | H | NH—CO—$NH_2$ | $CH_2$—O—$CH_2$—$CH(CH_3)_2$ |
| $CH_3$ | $CH_3$ | H | H | $NH_2$ | —$CH_2$—(1,3-dioxolan-2-yl) |
| $CH_3$ | $CH_3$ | H | H | NH—CO—NH—$C_2H_5$ | —$CH_2$—(1,3-dioxolan-2-yl) |
| $CH_3$ | $CH_3$ | $CH_3$ | H | $NH_2$ | $CH_2$—$OCH_3$ |
| $CH_3$ | $CH_3$ | H | H | $NH_2$ | $CH(C_2H_5)$—CO—$OCH_3$ |
| $CH_3$ | $CH_3$ | H | H | $NH_2$ | $CH(CH_3)$—O—N=C(CN)—CO—$OC_2H_5$ |
| $CH_3$ | $CH_3$ | H | H | NH—CO—$NH_2$ | $CH(C_2H_5)$—O—N=C—(CN)—CO—$OCH_3$ |
| $CH_3$ | $C_2H_5$ | H | H | NH—CO—$NH_2$ | $CH_2$—C≡CH |
| $CH_3$ | $C_2H_5$ | H | H | NH—CO—NH$(CH_2)_5$—CN | $CH_2$—$OC_2H_5$ |
| $CH_3$ | $C_2H_5$ | H | $CH_3$ | $OCH_3$ | $CH_2$—$OC_2H_5$ |
| $CH_3$ | $C_2H_5$ | H | H | $NH_2$ | $CH(CH_3)$—$CH_2$—$OCH_3$ |
| $CH_3$ | $C_2H_5$ | H | H | $OC_2H_5$ | $CH(CH_3)$—$CH_2$—$OCH_3$ |
| $CH_3$ | $C_2H_5$ | H | H | NH—CO—NH—$CH_3$ | $CH_2$—CO—$OCH(CH_3)_2$ |
| $C_2H_5$ | $C_2H_5$ | H | H | NH—CO—NH—$C_6H_{11}$ | $CH_2$—$OCH_3$ |
| $C_2H_5$ | $C_2H_5$ | H | H | NH—CO—NH—$(CH_2)_2$—$OCH_3$ | $CH_2$—$OCH_3$ |
| $C_2H_5$ | $C_2H_5$ | H | H | NH—CO—NH—$(CH_2)_2$—CO—$OCH_3$ | $CH_2$—O—n-$C_4H_9$ |
| $C_2H_5$ | $C_2H_5$ | H | H | NH—CO—NH—$CH_2$—cyclopropyl | $CH_2$—O—n-$C_4H_9$ |
| $C_2H_5$ | $C_2H_5$ | H | H | NH—CO—$NH_2$ | $CH_2$—$CH_2$—O—n-$C_3H_7$ |
| $C_2H_5$ | $C_2H_5$ | H | H | $OC_2H_5$ | $CH_2$—$CH_2$—O—n-$C_3H_7$ |
| $C_2H_5$ | $C_2H_5$ | H | H | $NH_2$ | $CH_2$—CO—$OC_2H_5$ |
| $C_2H_5$ | $C_2H_5$ | H | H | NH—CO—NH—$(CH_2)_2$—$OCH_3$ | $CH_2$—CO—$OC_2H_5$ |
| $CH_3$ | t-$C_4H_9$ | H | H | $OCH_3$ | $CH_2$—O—n-$C_4H_9$ |
| $CH_3$ | t-$C_4H_9$ | H | $CH_3$ | $NH_2$ | $CH_2$—O—n-$C_4H_9$ |
| $CH_3$ | $CH_3$ | H | H | $OC_2H_5$ | —$CH_2$—N(pyrazol-1-yl) |
| $CH_3$ | $CH_3$ | H | H | NH—CO—NH—$C_2H_5$ | —$CH_2$—N(pyrazol-1-yl) |

-continued
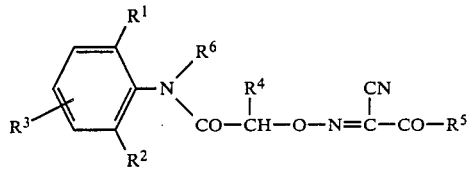
| $R^1$ | $R^2$ | $R^3$ | $R^4$ | $R^5$ | $R^6$ |
|---|---|---|---|---|---|
| CH₃ | CH₃ | CH₃ | H | NH₂ | 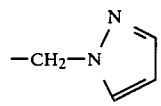 |
| CH₃ | CH₃ | CH₃ | H | OCH₃ | 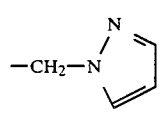 |
| CH₃ | C₂H₅ | H | H | NH—CO—NH—CH₃ | 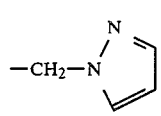 |
| CH₃ | C₂H₅ | H | H | NH—CO—NH—C₂H₅ | 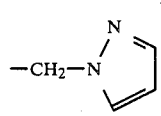 |
| CH₃ | CH₃ | H | H | NH₂ | 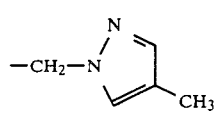 |
| CH₃ | CH₃ | H | H | OCH₃ | 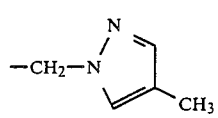 |
| CH₃ | C₂H₅ | H | H | NH₂ | 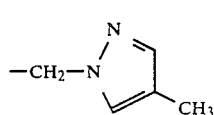 |
| CH₃ | C₂H₅ | H | H | NH—CO—NH₂ | 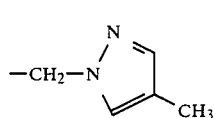 |
| CH₃ | CH₃ | H | H | NH—CO—NH₂ | 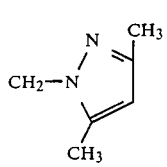 |
| CH₃ | CH₃ | H | H | OC₂H₅ | 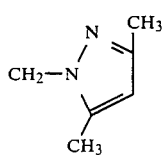 |
| CH₃ | CH₃ | H | H | NH—CO—NH₂ | 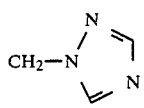 |

-continued $$\text{(I)}$$

[Structure of formula (I): substituted phenyl with R¹, R², R³ substituents, N–R⁶ group, and –CO–CH(R⁴)–O–N=C(CN)–CO–R⁵ chain]

| R¹ | R² | R³ | R⁴ | R⁵ | R⁶ |
|---|---|---|---|---|---|
| CH₃ | CH₃ | H | H | NH—CO—NH—C₆H₁₁ | CH₂—N(triazolyl) |
| CH₃ | CH₃ | H | H | O—n-C₄H₉ | CH₂—N(triazolyl) |
| CH₃ | CH₃ | H | H | NH—CO—NH₂ | CH₂—O—N=C(CN)CO—NH₂ |
| CH₃ | CH₃ | H | H | NH—CO—NH—CH₃ | CH₂—O—N=C(CN)CO—OCH₃ |
| C₂H₅ | C₂H₅ | H | H | OCH₃ | CH₂—O—N=C(CN)CO—NH₂ |
| C₂H₅ | C₂H₅ | H | H | OC₂H₅ | CH₂—O—N=C(CN)CO—NH₂ |

If in reaction variant (a), for example, N-n-butylthiomethyl-N-(2,6-dimethylphenyl)-2-chloroacetamide and ethyl 2-cyano-2-oximinoacetate are used as starting materials and N-ethyl-N,N-diisopropylamine is used as the proton acceptor, the course of the reaction can be represented by the following equation:

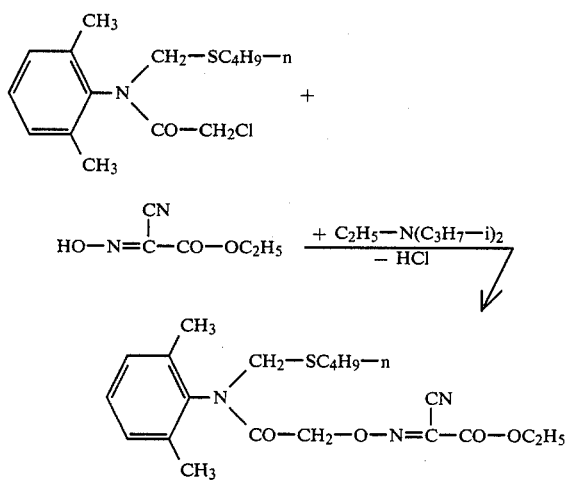

If in reaction variant (b), for example, 2-cyano-2-[N-(n-butylthiomethyl)-N-(2,6-dimethylphenyl)-aminocarbonylmethoximino]-acetamide and n-propyl isocyanate are used as starting materials and sodium hydride is used as the base, the course of the reaction can be represented by the following equation:

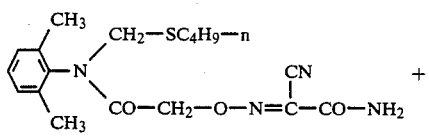

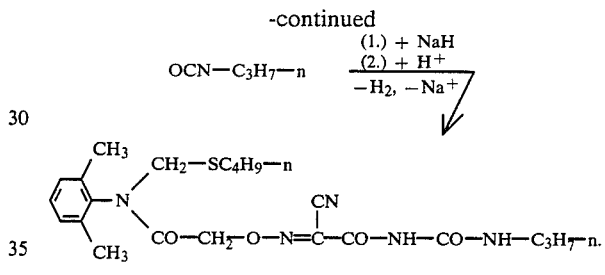

If, for example, N-chloromethyl-N-chloroacetyl-2,6-dimethyl-aniline and methyl 2-cyano-2-oximinoacetate as starting materials and triethylamine, as the proton acceptor, are used in reaction variant (c), the course of the reaction can be represented by the following equation:

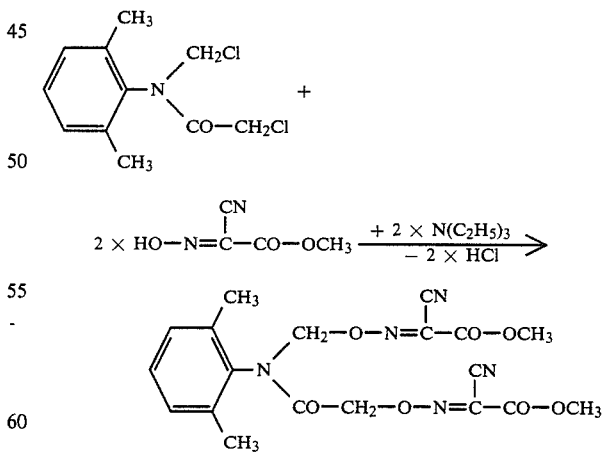

Preferred substituted acetanilides of formula (II) to be employed as starting materials in carrying out process variant (a) are those in which radicals R¹ to R⁴, R⁶ and X have the meanings which have already been mentioned in connection with preferred and particularly preferred compounds of formula (I).

The substituted acetanilides of the formula (II) are known, or can be obtained by processes which are known in principle, for example by reacting N-substituted anilines with acid-halides, or by reacting secondary acetanilides with compounds of the structure

wherein X and $R^6$ have the above meanings, if appropriate under phase-transfer conditions (see, for example, European Pat. No. 29,011, U.S. Pat. No. 3,997,326, German Patent Specification No. 2,328,340 and DE-OS (German Published Specification) No. 2,405,510).

Some of the compounds having the structure

are new, as are the corresponding precursors of these, and form a further subject of the present invention.

In particular, the present invention further provides, as a new intermediate compound, the compound of the formula

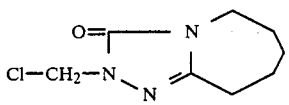

which can be prepared from the corresponding hydroxymethyl compound, which is likewise new, and a subject of the present invention, by reaction with thionyl chloride.

The compounds of the formula (IIa)

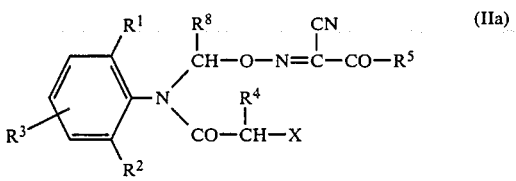

in which $R^1$, $R^2$, $R^3$, $R^4$, $R^5$, $R^8$ and X have the above meanings, which compounds are required, inter alia, as starting materials in reaction variant (a), can be obtained, for example, by reacting a compound of the general formula

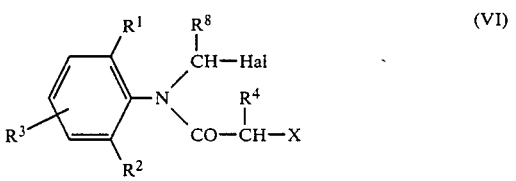

in which $R^1$, $R^2$, $R^3$, $R^4$, $R^8$, Hal and X have the above meanings, with a 2-cyano-2-oximinoacetic acid derivative of the formula (III) and a proton acceptor (such as triethylamine) in an inert solvent (such as acetonitrile or toluene) at a low temperature, for example at −20° to 0° C.

Preferred 2-cyano-2-oximino-acetic acid derivatives of formula (II) furthermore to be used in carrying out reaction variants (a) and (c) are those in which the radical $R^5$ has the meaning given in the definition of preferred and particularly preferred compounds of formula (I).

The majority of the compounds of formula (III) are known, or they can be prepared according to known processes (see Ber. 42, 736–741 (1909); 54, 1334 (1921); and U.S. Pat. No. 4,188,401).

Thus, for example, an oximated urea of the general formula

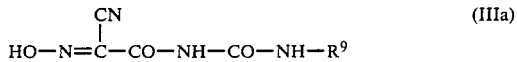

in which $R^9$ has the meaning given above, is obtained when an isocyanate of the general formula

in which $R^9$ has the meaning given above, is reacted in a first stage with ammonia to give N-substituted urea, this product is converted in a second stage with cyanoacetic acid, in the presence of acetic anhydride, to the corresponding 1-substituted 3-(2-cyanoacetyl)-urea, and this product is reacted further with nitrous acid to give the corresponding oximated urea.

The compounds of the formula (IV) which are required in carrying out reaction variant (b) can be prepared from compounds of formulae (II) and (III), by the method described above.

The isocyanates of the formula (V) in reaction variant (b) which are likewise required are known compounds, and can be prepared in a customary manner, for example by reacting primary amines with phosgene.

The compounds of the formula (IV) which are to be employed in carrying out reaction variant (c) can be obtained when an aniline is reacted with an aldehyde, by a process analogous to that already described further above, to give the Schiff bases, which are then reacted further with an acid-halide to give the compounds of the formula (VI) (see, for example, European Pat. No. 29,011).

Suitable diluents in reaction variant (a) are any of the organic solvents which are inert to the reactants, preferably polar solvents, for example acetonitrile, acetone, chloroform, benzonitrile, dimethylacetamide, dimethylformamide, dimethylsulphoxide, chlorobenzene, ethyl acetate, dioxane, methyl ethyl ketone, methylene chloride and tetrahydrofuran, and non-polar solvents, for example toluene.

The reaction can, if appropriate, also be carried out in mixtures of water and a water-miscible organic solvent, or in heterogeneous systems consisting of water and a solvent which is immiscible or only partially miscible with water.

The acid-binding agents used are organic bases, preferably tertiary amines, for example quinoline, dimethylbenzylamine, N,N-dimethylaniline, ethyldicyclohexylamine, ethyldiisopropylamine, picoline, pyridine and triethylamine, or the 2-cyano-2-oximinoacetic acid derivatives are employed in the form of their alkali metal salts or alkaline earth metal salts.

The reaction according to the invention is carried out at a temperature from 0° to 140° C., preferably from 60° to 110° C. When water is used individually or concomitantly as the diluent, the reaction is carried out at a temperature from the solidification point of the aqueous solution to +70° C., preferably from 40° to 60° C.

The process according to the invention can be carried out, for example, as follows:

A 2-cyano-2-oximinoacetic acid derivative of the formula (III), dispersed or dissolved in a diluent, is initially introduced, and the molar amount of a tertiary amine is added, it being possible for salt formation to take place. If an alkali metal salt or alkaline earth metal salt of the 2-cyano-2-oximinoacetic acid derivative is employed, it can be initially introduced into an inert solvent. To this is added the substituted acetanilide of the formula (II), preferably dissolved in a diluent. If necessary, a small amount of an iodide is added to the reaction mixture to obtain a more rapid reaction. After the end of the reaction, the substituted oximinoacetanilides are isolated in a customary manner, and, if required, are purified.

Inert anhydrous solvents, such as ethers, for example diisopropyl ether, dioxane or tetrahydrofuran, can be used as diluents in reaction variant (b).

The reaction is carried out at a temperature from $-20°$ to $80°$ C., preferably $20°$ to $60°$ C.

Alcoholates, for example alkali metal alcoholates, such as sodium methoxide and potassium tert.-butoxide, and metal hydrides, for example alkali metal hydrides, such as sodium hydride and potassium hydride, can be employed as bases.

Reaction variant (b) according to the invention can be carried out as follows:

A compound of the formula (IV) in a diluent is reacted with one of the abovementioned bases to give the corresponding anion of the amide, and this is reacted, in the temperature range given, with the isocyanate of the formula (V). After the reaction has ended, the cold mixture is rendered slightly acidic with an organic carboxylic acid, such as acetic acid.

The reaction of reaction variant (c) can likewise be carried out in one of the inert solvents mentioned above, in the presence of an acid-binding agent, as described under reaction variants (a) and (b), at an elevated temperature. The process is usually carried out as follows: a compound of the formula (VI) is reacted with at least 2 mols of a 2-cyano-2-oximinoacetic acid derivative of the formula (III) in the presence of a proton acceptor, for example, ethyl-diisopropylamine, in an inert solvent, for example acetonitrile, at an elevated temperature.

Depending on the reaction conditions, the active compounds according to the invention are precipitated in crystalline form, or they remain dissolved in the organic solvent and, after the solution has been washed with water, can then be separated out by careful concentration of the solution or by the addition of organic solvents of low polarity, such as cyclohexane, dibutyl ether, butyl acetate or carbon tetrachloride. If necessary, water-miscible solvents must be removed after the reaction by evaporating them off in vacuo.

If the compounds according to the invention are dissolved in a water-miscible solvent, they can, for example, also be precipitated by the addition of water. If permitted by the particular conditions of the working-up process, the solutions of the active compounds according to the invention, or the still solvent-moist suspensions of the active compounds, are rendered slightly acidic.

The compounds according to the invention can decompose at a relatively high temperature, so that it is not always possible to determine the melting points exactly.

The active compounds according to the invention exhibit a powerful microbicidal action and can be employed in practice for combating undesired microorganisms. The active compounds are suitable for use as plant protection agents.

Fungicidal agents in plant protection are employed for combating Plasmodiophoromycetes, Oomycetes, Chytridiomycetes, Zygomycetes, Ascomycetes, Basidiomycetes and Deuteromycetes.

The good toleration, of plants, of the active compounds, at the concentrations required for combating plant diseases, permits treatment of above-ground parts of plants, of vegetative propagation stock and seeds and of the soil.

As plant protection agents, the active compounds according to the invention can be used with particularly good success for combating Oomycetes, for example against the blight and late blight of potato and tomato causative organism (Phytophthora infestans).

They exhibit a high curative and protective activity. In addition, good actions against bacteria are found.

The active compounds according to the invention not only have the good properties of outstanding commercial preparations, but in addition also possess substantial advantages. These consist primarily in the ability of the substances according to the invention to penetrate the plants. They can be taken up by the seed surface, by the roots and also by above-ground organs of plants after external applications. They also possess the advantageous ability to act locosystemically, that is to say to exercise an in-depth action in the plant tissue and thereby to eliminate fungal pathogens which have already penetrated the tissue of the host plant.

The active compounds can be converted to the customary formulations, such as solutions, emulsions, suspensions, powders, foams, pastes, granules, aerosols, natural and synthetic materials impregnated with active compound, very fine capsules in polymeric substances and in coating compositions for seed, and formulations used with burning equipment, such as fumigating cartridges, fumigating cans and fumigating coils, as well as ULV cold mist and warm mist formulations.

These formulations may be produced in known manner, for example by mixing the active compounds with extenders, that is to say liquid or liquefied gaseous or solid diluents or carriers, optionally with the use of surface-active agents, that is to say emulsifying agents and/or dispersing agents and/or foam-forming agents. In the case of the use of water as an extender, organic solvents can, for example, also be used as auxiliary solvents.

As liquid diluents or carriers, especially solvents, there are suitable in the main, aromatic hydrocarbons, such as xylene, toluene or alkyl naphthalenes, chlorinated aromatic or chlorinated aliphatic hydrocarbons, such as chlorobenzenes, chloroethylenes or methylene chloride, aliphatic or alicyclic hydrocarbons, such as cyclohexane or paraffins, for example mineral oil fractions, alcohols, such as butanol or glycol as well as their ethers and esters, ketones, such as acetone, methyl ethyl ketone, methyl isobutyl ketone or cyclohexanone, or strongly polar solvents, such as dimethylformamide and dimethylsulphoxide, as well as water.

By liquefied gaseous diluents or carriers are meant liquids which would be gaseous at normal temperature and under normal pressure, for example aerosol propellants, such as halogenated hydrocarbons as well as butane, propane, nitrogen and carbon dioxide.

As solid carriers there may be used ground natural minerals, such as kaolins, clays, talc, chalk, quartz, attapulgite, montmorillonite or diatomaceous earth, and ground synthetic minerals, such as highly-dispersed silicic acid, alumina and silicates. As solid carriers for granules there may be used crushed and fractionated natural rocks such as calcite, marble, pumice, sepiolite and dolomite, as well as synthetic granules of inorganic and organic meals, and granules of organic material such as sawdust, coconut shells, corn cobs and tobacco stalks.

As emulsifying and/or foam-forming agents there may be used non-ionic and anionic emulsifiers, such as polyoxyethylene-fatty acid esters, polyoxyethylene-fatty alcohol ethers, for example alkylaryl polyglycol ethers, alkyl sulphonates, alkyl sulphates, aryl sulphonates as well as albumin hydrolysis products. Dispersing agents include, for example, lignin sulphite waste liquors and methylcellulose.

Adhesives such as carboxymethylcellulose and natural and synthetic polymers in the form of powders, granules or latices, such as gum arabic, polyvinyl alcohol and polyvinyl acetate, can be used in the formulations.

It is possible to use colorants such as inorganic pigments, for example iron oxide, titanium oxide and Prussian Blue, and organic dyestuffs, such as alizarin dyestuffs, azo dyestuffs or metal phthalocyanine dyestuffs, and trace nutrients, such as salts of iron, manganese, boron, copper, cobalt, molybdenum and zinc.

The formulations in general contain from 0.1 to 95 percent by weight of active compound, preferably from 0.5 to 90 percent by weight.

The active compounds according to the invention can be present in the formulations or in the various use forms as a mixture with other known active compounds, such as fungicides, bactericides, insecticides, acaricides, nematicides, bird repellents, growth factors, plant nutrients and agents for improving soil structure.

The active compounds can be used as such or in the form of their formulations or the use forms prepared therefrom by further dilution, such as ready-to-use solutions, emulsions, suspensions, powders, pastes and granules. They are used in the customary manner, for example by watering, immersion, spraying, atomizing, misting, vaporizing, injecting, forming a slurry, bruching on, dusting, scattering, dry dressing, moist dressing, wet dressing, slurry dressing or encrusting.

Especially in the treatment of parts of plants, the active compound concentrations in the use forms can be varied within a substantial range. They are, in general, between 1 and 0.001% by weight, preferably between 0.5 and 0.001%.

In the treatment of seed, amounts of active compound of 0.001 to 50 g per kilogram of seed, preferably 0.01 to 10 g, are generally required.

For the treatment of soil, active compound concentrations of 0.00001 to 0.1% by weight, preferably 0.0001 to 0.02%, are generally required at the place of action.

The present invention also provides fungicidal compositions containing as active ingredient a compound of the present invention in admixture with a solid or liquefied gaseous diluent or carrier or in admixture with a liquid diluent or carrier containing a surface-active agent.

The present invention also provides a method of combating fungi which comprises applying to the fungi, or to a habitat thereof, a compound of the present invention alone or in the form of a composition containing as active ingredient a compound of the present invention in admixture with a diluent or carrier.

The present invention further provides crops protected from damage by fungi by being grown in areas in which immediately prior to and/or during the time of the growing a compound of the present invention was applied alone or in admixture with a diluent or carrier.

It will be seen that the usual methods of providing a harvested crop may be improved by the present invention.

PREPARATIVE EXAMPLES

EXAMPLE 1

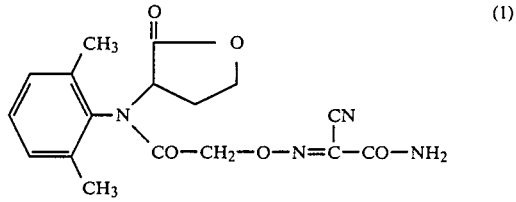

(1)

7.91 g of 2-cyano-2-oximinoacetamide and 200 g of dimethylsulphoxide were initially introduced, and 7.1 g of triethylamine were added. After 30 minutes, 20.6 g of N-(tetrahydrofuran-2-on-3-yl)-N-(2,6-dimethylphenyl)-2-chloroacetamide were added, and the mixture was kept at 115° C. for 7 hours. The reaction was monitored by thin layer chromatography on silica gel 60 F 254-mobile phase: acetic acid/ethyl acetate/toluene. The bulk of the dimethylsulphoxide was then distilled off at 0.2 mbar. Ethyl acetate and water were added to the distillation residue. The ethyl acetate solution was washed 3 times with water, dried over sodium sulphate and evaporated down in vacuo. The distillation residue crystallized with diisopropyl ether. 20.8 g of 2-cyano-2-(N-(2,6-dimethylphenyl)-N-(tetrahydrofuran-2-on-3-yl)-amino-carbonylmethyloximino)-acetamide of melting point 201° to 203° C. were obtained. When recrystallized from toluene/diethyl ketone (7:1), the compound melted at 203° to 204° C.

The following compounds of the formula (I) were prepared analogously:

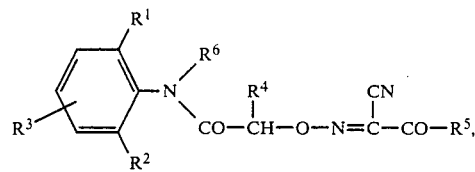

| Example No. | $R^1$ | $R^2$ | $R^3$ | $R^4$ | $R^5$ | $R^6$ | Melting point °C. | Reaction conditions |
|---|---|---|---|---|---|---|---|---|
| 2 | $CH_3$ | $CH_3$ | H | H | $NH_2$ | $-CH_2-OCH_3$ | 151.5 | 6 hours 80° acetonitrile |
| 3 | $C_2H_5$ | $C_2H_5$ | H | H | $NH_2$ | $-CH_2-OCH_3$ | 109 | 7 hours 80° acetonitrile |
| 4 | $C_2H_5$ | $C_2H_5$ | H | H | $NH_2$ | $-CH_2-O-N=C(CN)-CO-NH_2$ | 161 | 7 hours 80° acetonitrile |
| 5 | $CH_3$ | $CH_3$ | H | H | $NH_2$ | $-CH_2-O-N=C(CN)-CO-NH_2$ | 228 | 7 hours 80° acetonitrile |

-continued

| Example No. | R¹ | R² | R³ | R⁴ | R⁵ | R⁶ | Melting point °C. | Reaction conditions |
|---|---|---|---|---|---|---|---|---|
| 6 | CH₃ | CH₃ | H | H | NH₂ | —CH₂—C(C₂H₅)(CH₂O)(CH₂O) (5-ethyl-1,3-dioxan-5-yl-methyl) | 167 | 7 hours 80° acetonitrile |
| 7 | CH₃ | CH₃ | H | H | NH₂ | —CH₂—N(N=)—C(O)—N—(CH₂)₅ | 95 | 7 hours 80° acetonitrile |
| 8 | CH₃ | CH₃ | H | CH₃ | NH₂ | —CH₂—OCH₃ | 137 | 5 hours 117° DMSO |
| 9 | CH₃ | CH₃ | H | H | NH₂ | —CH(CH₃)—CO—OCH₃ | 171.5 | 5 hours 116° DMSO |
| 10 | C₂H₅ | C₂H₅ | H | H | NH₂ | —CH(CH₃)—CO—OCH₃ | 102 | 5 hours 110° DMSO |
| 11 | CH₃ | CH₃ | H | H | NH₂ | CH₂—N(imidazolyl) | 201.5 | 6 hours 80° acetonitrile |
| 12 | CH₃ | CH₃ | H | H | NH₂ | CH—N(pyrazolyl) | 176 | 6 hours 80° acetonitrile |
| 13 | CH₃ | CH₃ | H | H | NH₂ | —CH(CH₃)—CO—OCH(CH₃)₂ | 92 | 4 hours 115° DMF |

EXAMPLE 13

Preparation of the intermediate product for Example 6

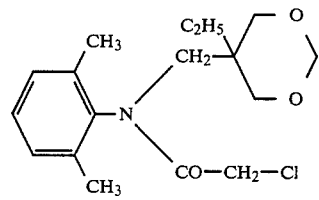

(a) 6.4 g of chloroacetyl chloride were added at 5° C., to 19.9 g of N-((5-ethyl-1,3-dioxan-5-yl)-methyl)-2,6-dimethylaniline, dissolved in 50 ml of chlorobenzene. The mixture was kept at 80° C. for 2 hours, and 3.2 g of chloroacetyl chloride were again added at intervals of 1 hour. Finally, the mixture was left for a further 5 hours at 100° C. It was evaporated down in vacuo, the residue was dissolved in xylene, and the solution was washed twice with water, with the addition of a little aceitic acid. The xylene solution was dried over sodium sulphate, stirred optimally with "Tonsil" twice and evaporated down in vacuo. The residue—22.6 g—crystalli ed slowly; it was treated with petroleum ether. The crystals were dried in vacuo at 60° C. Crystals of melting point 99° C. were obtained, and the IR spectrum (CHCl₃) showed an N—CO band at 1680 cm⁻¹.

(b) Preparation of the precursor:

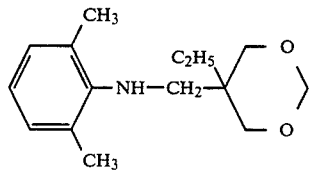

A mixture of 82.3 g of 5-ethyl-1,3-dioxan-5-yl-methyl toluenesulphonate, 106 g of dimethylformamide, 121 g of 2,6-dimethylaniline and 40 g of potassium carbonate was heated at 163° to 169° C. for 16 hours. The reaction mixture was then diluted with toluene, washed with water and evaporated down in vacuo, and the residue was distilled. The fraction at 126° C./0.04 mbar contained 11.6 g of N-((5-ethyl-1,3-dioxan-5-yl)-methyl)-2,6-dimethylaniline.

EXAMPLE 14

Preparation of the intermediate product for Example 7

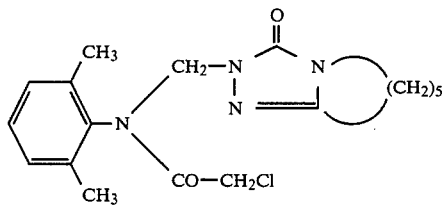

(a) A mixture of 19.8 g of N-chloroacetyl-2,6-dimethylaniline, 200 ml of methylene chloride, 100 ml of 45% strength sodium hydroxide solution, 0.5 g of tetrabutylammonium chloride and 22.5 g of 2-chloromethyl-3-oxo-4,5-pentamethylene-1,2,4-triazoline-5 was stirred rapidly for 4½ hours at 40° C. 600 ml of toluene were added, and the mixture was washed several times with water, dried over sodium sulphate and then treated optimally with "Tonsil". It was evaporated down in vacuo. The residue from evaporation was dissolved in 600 ml of hot xylene, and a mixture of 100 ml of dibutyl ether and 200 ml of petroleum ether was added to the solution.

N-(2,6-Dimethylphenyl)-N-(3-oxo-4,5-pentamethylene-1,2,4-triazol-(5)-in-2-yl-methyl)-chloroacetamide crystallized out. It was separated off, washed with petroleum ether and dried. The compound had a melting point of 128° C.

(b) Preparation of the precursor:

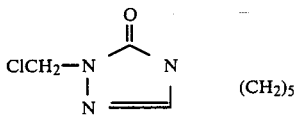

29 g of thionyl chloride were added to a solution of 21.7 g of 2-hydroxymethyl-3-oxo-4,5-pentamethylene-1,2,4-triazoline(5) in 50 ml of chloroform and one drop of dimethylformamide, at 3° C. The mixture was allowed to stand for 4 hours without being cooled, and was evaporated down in vacuo. The solid residue was dried at 30° C./0.1 mbar. 23.3 g of 2-chloromethyl-3-oxo-4,5-pentamethylenetriazoline(5) were obtained.

(c) Preparation of the starting material:

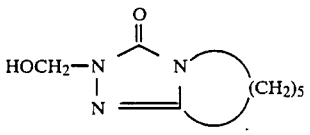

199 g of 4,5-pentamethylene-1,2,4-triazol(5)in-3-one were introduced, in 5 portions, into 290 g of 24.2% strength formalin solution, at 24° C. The mixture was stirred for 3½ hours and filtered, and the filtrate was diluted with 120 ml of water and extracted with 3×300 ml of chloroform. The chloroform solution was dried over sodium sulphate and evaporated down in vacuo, and the residue was dried at 60° C./0.1 mbar. 204.8 g of 2-hydroxymethyl-3-oxo-4,5-pentamethylene-1,2,4-triazoline-(5) of melting point 104° C. were obtained.

The fungicidal activity of the compounds of this invention is illustrated by the following biotest example.

The known comparison compound is identified as follows:

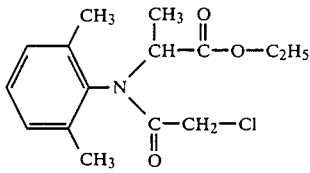

EXAMPLE A

Phytophthora test (tomato)/protective

Solvent: 4.7 parts by weight of acetone
Emulsifier: 0.3 parts by weight of alkylaryl polyglycol ether To produce a suitable preparation of active compound, 1 part by weight of active compound was mixed with the stated amounts of solvent and emulsifier, and the concentrate was diluted with water to the desired concentration.

To test for protective activity, young plants were sprayed with the preparation of active compound until dripping wet. After the spray coating had dried on, the plants were inoculated with an aqueous spore suspension of Phytophthora infestans.

The plants were placed in an incubation cabinet at 100% relative atmospheric humidity and at about 20° C.

Evaluation was carried out 3 days after the inoculation.

In this test, the compounds according to the invention were clearly superior to the compounds of the prior art.

It is understood that the specification and examples are illustrative but not limitative of the present invention and that other embodiments within the spirit and scope of the invention will suggest themselves to those skilled in the art.

We claim:

1. A substituted oximinoacetanilide of the formula

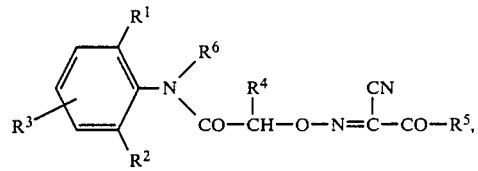

in which
$R^1$ denotes an alkyl or alkoxy group having 1 to 4 carbon atoms or a halogen atom,
$R^2$ denotes a hydrogen or halogen atom or an alkyl group having 1 to 4 carbon atoms or trifluoromethyl group,
$R^3$ denotes a hydrogen or halogen atom or an alkyl group having 1 to 4 carbon atoms,
$R^4$ denotes a hydrogen atom or a methyl group,
$R^5$ denotes an alkoxy group having 1 to 4 carbon atoms, amino or —NH—CO—NH—$R^7$ group,
wherein
$R^7$ is a hydrogen atom or an optionally cyano-, $C_1$-$C_4$-alkoxy- or alkoxycarbonyl-substituted $C_1$-$C_{15}$-alkyl group, or represents a $C_3$-$C_6$-cycloalkyl group, and
$R^6$ denotes a $C_3$ to $C_5$ alkinyl, $C_1$ to $C_4$ alkoxy-$C_1$ to $C_3$ alkyl, halogeno-$C_1$ to $C_4$ alkoxy-$C_1$ to $C_3$ alkyl, cyano-$C_1$ to $C_4$ alkoxy-$C_1$ to $C_3$ alkyl, $C_4$ to $C_7$ cyclo-alkoxy-$C_1$ to $C_3$ alkyl, $C_2$ to $C_4$ alkenoxy-$C_1$ to $C_3$ alkyl, $C_2$ to $C_4$ alkinoxy-$C_1$ to $C_3$ alkyl, $C_1$ to $C_4$ alkylthio-$C_1$ to $C_3$ alkyl, ($C_1$ to $C_4$ alkyl)carbonyl-$C_1$ to $C_3$ alkyl, ($C_1$ to $C_4$ alkoxy)carbonyl-$C_1$ to $C_3$ alkyl or ($C_1$ to $C_4$ alkylthio)carbonyl-$C_1$ to $C_3$ alkyl group; denotes an aminocarbonyl-$C_1$ to $C_3$ alkyl group, wherein the amino group thereof is optionally substituted by 1 to 2 $C_1$ to $C_3$ alkyl radicals; denotes

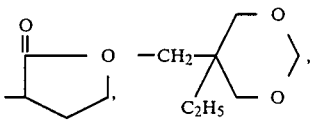

-continued

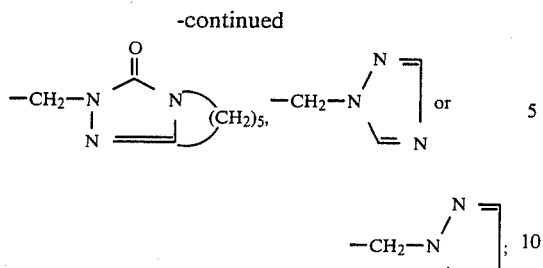

or denotes a radical of the general formula

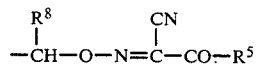

wherein $R^8$ is a hydrogen atom or a methyl or ethyl group.

2. A compound according to claim 1, in which $R^1$ represents an alkyl group having 1 to 4 carbon atoms or an alkoxy group having 1 to 4 carbon atoms or a chlorine atom, $R^2$ represents a hydrogen atom, an alkyl group having 1 to 4 carbon atoms or a chlorine atom, $R^3$ and $R^4$ represent hydrogen atoms, $R^5$ represents an alkoxy group having 1 to 3 carbon atoms or represents an amino group, and $R^6$ denotes a $C_3$ to $C_5$ alkinyl, $C_1$ to $C_4$ alkoxy-$C_1$ to $C_3$ alkyl, $C_1$ to $C_4$-alkylthio-$C_1$ to $C_3$ alkyl, halogeno-$C_1$ to $C_4$ alkoxy-$C_1$ to $C_3$ alkyl, cyano-$C_1$ to $C_3$ alkoxy-$C_1$ to $C_3$ alkyl, $C_4$ to $C_7$ cycloalkoxy-$C_1$ to $C_3$ alkyl, $C_2$ to $C_4$ alkenoxy-$C_1$ to $C_3$ alkyl, $C_2$ to $C_4$ alkinoxy-$C_1$ to $C_4$ alkyl, methycarbonyl-methyl, methoxycarbonyl-$C_1$ to $C_3$ alkyl or methylthiocarbonyl-$C_1$ to $C_3$ alkyl group; denotes an aminocarbonyl-$C_1$ to $C_3$ alkyl group wherein the amino group thereof is optionally substituted by 1 or 2 methyl radicals; denotes

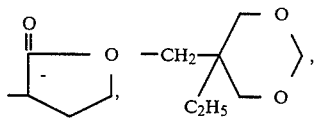

or denotes a methoxycarbonyl-(cyano)-methyleneiminoxymethyl or aminocarbonyl-(cyano)-methyleneiminoxymethyl radical.

3. A compound according to claim 1, wherein such compound is 2-cyano-2-((N-(2,6-dimethylphenyl)-N-(methoxymethyl)-1-amino-carbonyl)-ethoximino)-acetamide of the formula

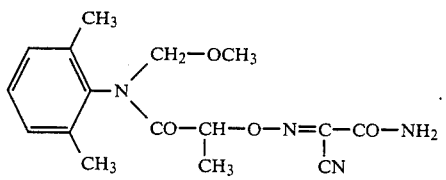

4. A compound according to claim 1, wherein such compound is 2-cyano-2-((N-(2,6-dimethylphenyl)-N-(1-methoxycarbonyl-ethyl)-amino-carbonyl)-methoximino)-acetamide of the formula

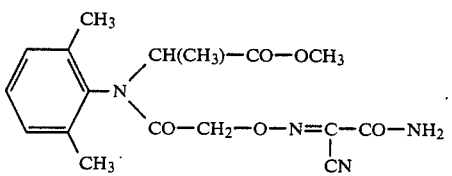

5. A fungicidal composition comprising a fungicidally effective amount of a compound according to claim 1 in admixture with a diluent.

6. A method of combating fungi comprising applying to the fungi, or to a habitat thereof, a fungicidally effective amount of a compound according to claim 1.

7. The method according to claim 6 wherein such compound is 2-cyano-2-((N-(2,6-dimethyl)-N-(methoxymethyl)-1-amino-carbonyl)-ethoximino)-acetamide or 2-cyano-2-((N-(2,6-dimethylphenyl)-N-(1-methoxycarbonyl-ethyl)-amino-carbonyl)-methoximino)-acetamide.

* * * * *

UNITED STATES PATENT AND TRADEMARK OFFICE
CERTIFICATE OF CORRECTION

PATENT NO. : 4,537,905

DATED : August 27, 1985

INVENTOR(S) : Wilhelm Brandes, et al.

It is certified that error appears in the above-identified patent and that said Letters Patent is hereby corrected as shown below:

| | |
|---|---|
| Col. 12, line 3 | Delete "42" and "54" and substitute --42-- and --54-- |
| Col. 12, line 32 | Delete "(IV)" and substitute --(VI)-- |
| Col. 14, line 7 | Before "plants" delete "of" and substitute --by-- |
| Col. 16, line 45 | Delete "carbonylmethyloximino" and substitute --carbonylmethoximino-- |
| Col. 17, line 60 | Delete "aceitic" and substitute --acetic-- |
| Col. 20, line 47 | Delete "$C_{15}$" and substitute --$C_5$-- |
| Col. 21, line 40 | Delete "$C_4$" and substitute --$C_3$-- |

Signed and Sealed this

Twenty-eighth Day of January 1986

[SEAL]

Attest:

DONALD J. QUIGG

Attesting Officer

Commissioner of Patents and Trademarks